United States Patent [19]

Fink

[11] 4,219,021
[45] Aug. 26, 1980

[54] MULTI-POSITION STOP-COCK VALVE FOR INTRAVENOUS ADMINISTRATION OF MULTIPLE MEDICATIONS

[76] Inventor: Joseph L. Fink, 1761 Seneca La., Las Vegas, Nev. 89109

[21] Appl. No.: 881,393

[22] Filed: Feb. 27, 1978

[51] Int. Cl.² .............................................. A61M 5/00
[52] U.S. Cl. .............................. 128/214 B; 128/274; 137/556.6; 137/625.41
[58] Field of Search ............ 137/551, 555, 556, 556.6, 137/625.41; 128/214 R, 214.2, 274, 214 B

[56] References Cited

U.S. PATENT DOCUMENTS 2,999,499  9/1961  Willet ................................ 128/214 R
3,021,840  2/1962  Hallamore et al. ................... 128/188
3,276,472  10/1966 Jinkins et al. ................. 137/625.41 X
3,783,900  1/1974  Waldbillig ........................ 137/625.47
3,934,576  1/1976  Danielsson ................... 128/214 R X
4,072,146  2/1978  Howes ............................. 128/214.4

Primary Examiner—Dalton L. Truluck
Attorney, Agent, or Firm—Morse, Altman, Oates & Bello

[57] ABSTRACT

Multi-position stop-cock valves for use in the intravenous administration of different medications are provided with integral color codes on the valve body and the valve handles whereby the valve position and the medication flow through the valve will be immediately apparent to the attendant.

10 Claims, 14 Drawing Figures

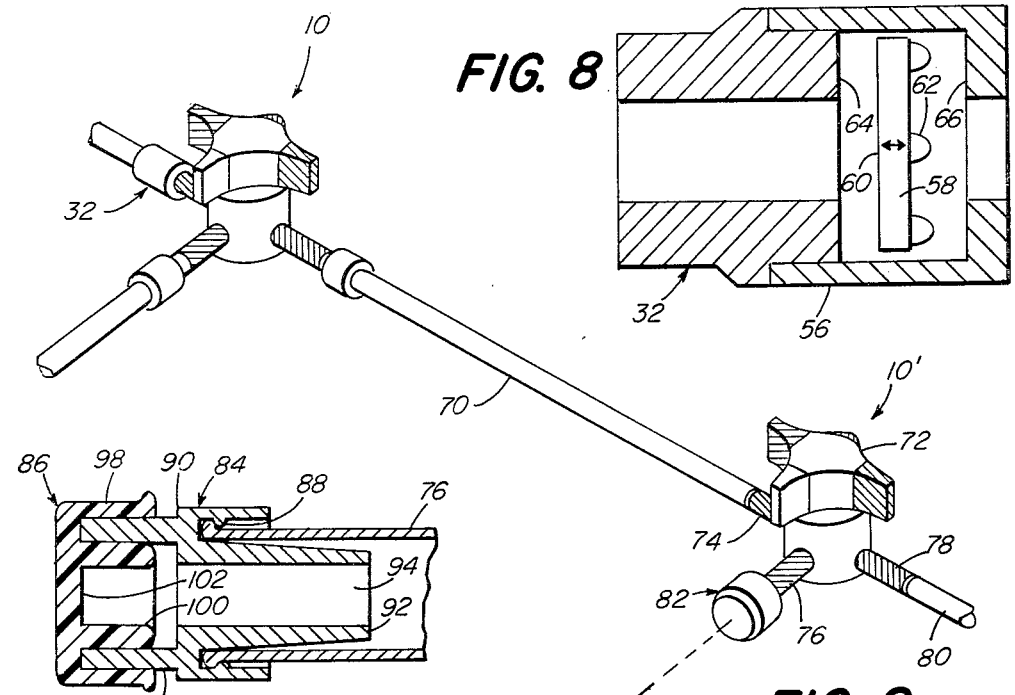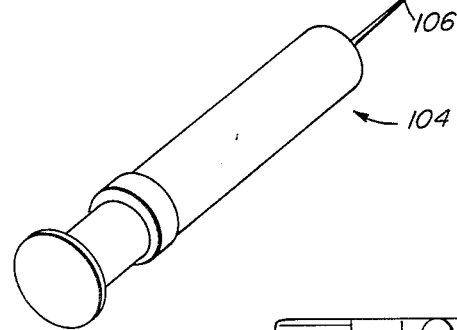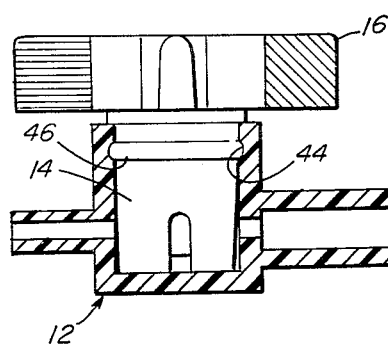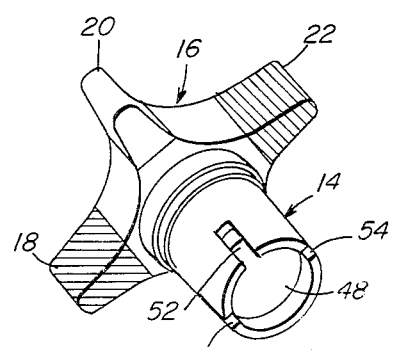

MULTI-POSITION STOP-COCK VALVE FOR INTRAVENOUS ADMINISTRATION OF MULTIPLE MEDICATIONS

BACKGROUND OF THE INVENTION

1. Field of the Invention

This invention relates generally to multi-position valves for use with intravenous sets and more particularly is directed towards a new and improved color-coded, multi-position valve whereby the valve position and flow paths through the valve may be immediately determined even at a distance.

2. Description of the Prior Art

It is common practice in treating patients, both under normal as well as emergency conditions, to introduce various medications intravenously through a tube system generally identified as an IV set. The sets typically involve one or more flexible plastic tubes connected to one or more containers of liquid medications which flow directly into the patient through a needle inserted in the vein of the patient. Where a single medication is being administered, it is necessary to control only the flow rate of the medication. However, in many instances, particularly during the course of an operation, several medications are administered, sometimes in a certain sequence and sometimes simultaneously, through the same IV system. To accommodate the different medications, the IV set is provided with multi-position valves which connect the several containers, each of a particular medication, and the different medications are then adminstered by manipulation of the valve. The valve normally employs a rotatable core which will connect different lines to the patient depending upon the position of the valve.

The primary difficulty encountered with this type of valve is that it is not immediately obvious to the attendant as to which liquid is flowing and which is stopped. The valves normally will be marked with arrows or directions printed or molded directly onto the valve. These indicia are usually quite small and confusing and, unless the operator is using the same type of valve on a frequent and regular basis, he or she may make an error, especially if under the pressure of an emergency situation.

Accordingly, it is an object of the present invention to provide improvements in valves used in IV sets. Another object of this invention is to provide a means for readily identifying the position of a valve and the flow paths in a multi-position valve unit. Still another object of this invention is to provide a color-coded, multi-position valve which may be used singly or in sets for selectively administering multiple medications to patients as well as for sampling venous blood without disrupting the set.

SUMMARY OF THE INVENTION

This invention features a color-coded stop-cock valve for use with IV sets comprising a valve body having at least two inlets and one outlet adapted to be connected to an IV system, a rotatable valve core formed with passages to interconnect with the inlet and outlet passages in the valve body upon rotation thereof and a valve handle drivingly connected to the core. The handle and the valve body are marked with distinct colored indicia unique to each inlet and outlet whereby the position of the valve and the flow arrangement can be immediately ascertained by color matching the handle to the valve body.

This invention also features a ganged pair of multi-position stop-cock, color-coded valves adapted to deliver one or more liquid medications intravenously to a patient as well as to allow blood sampling from the same system without producing any backflow or dilution of the sample. The first valve is connected to the intravenous medication supply and the second valve is proximate to the injection site and provided with a rubber cap over one of the inlet connections, with check valves provided to allow liquids to flow in one direction only. A venous blood sample is obtained by turning off the valve to prevent flow and using a syringe inserted through the cap to extract blood from the patient.

BRIEF DESCRIPTION OF THE DRAWINGS

FIG. 6 is a sectional view in side elevation of the valve, FIG. 7 is a view in perspective showing the valve core and handle portion of the valve, FIG. 8 is a detail sectional view of the check valve, FIG. 9 is a view in perspective showing the ganged valve system, FIG. 10 is a detail sectional view of the injection cap employed in the FIG. 9 embodiment.

DETAILED DESCRIPTION OF THE PREFERRED EMBODIMENTS

Figure 1:
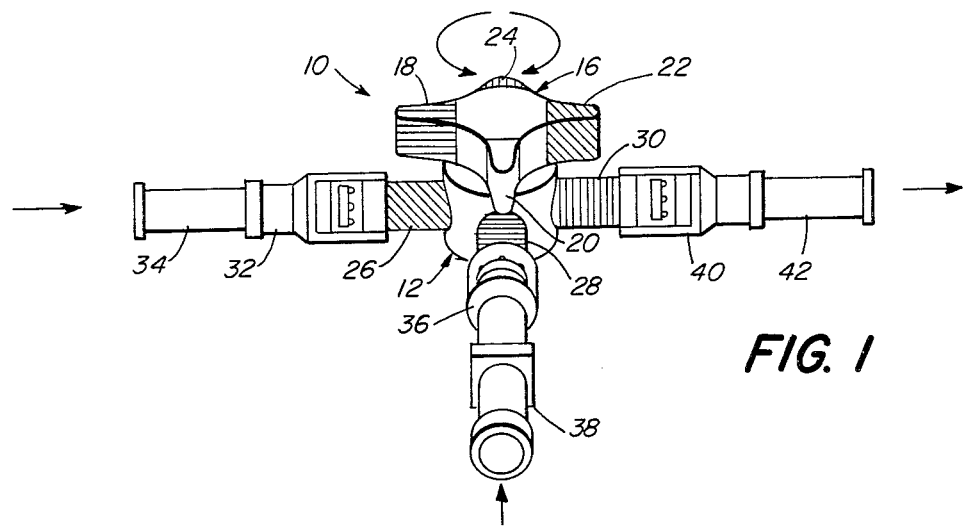
FIG. 1 is a view in perspective of a color-coded, multi-position valve made according to the invention.

Referring now to the drawings and to FIG. 1 in particular, the reference character 10 generally indicates a color-coded, four-way stop cock valve for use primarily with an IV set for administering at least two different liquid medications to a patient. An IV set typically is comprised of a container, such as a bottle or plastic bag, containing a quantity of an intravenous fluid connected to the patient through a drop chamber and to a length of plastic tubing which, in turn, connects to a needle inserted in the vein of the patient. The rate of fluid flow into the patient is controlled by various means which typically involves pinching the tubing to a greater or lesser extent as by a clamp or the like. Normally the bottle is provided with a hook and is suspended from a suitable support at an elevated position above the patient, with the flow of the medication being by gravity through the IV set.

In many instances, treatment of the patient requires the administration of two different liquid medications and, rather than subject the patient to the discomfort of additional needle insertions, the secondary intranvenous liquid is fed to the primary IV set by means of a secondary set through a multi-position valve. The valve serves to control the flow path to the patient and may selectively open and close flow paths from both the primary and secondary sets so that the patient will receive either one, both or neither of the medications.

Heretofore it has been difficult for doctors, nurses and attendants in change of the administration of the IV medication to quickly determine with certainty the flow paths of the different medications. The operation of valves of this type has been difficult to understand since their valve positions have not been readily apparent without reference to printed directions or to arrows or other indicia on the valve, which markings may be ambiguous. In any event, errors happen rather frequently because of the uncertainty as to the flow paths of the medication through the valve. Also, multi-position valves of this type have had the further disadvantage of causing the unintentional mixing of medications when the valve is in an off position. Mixing results when the liquid from one set flows into the other set because of a pressure differential between the set sets.

The foregoing problems have been overcome by the valve 10 of FIG. 1, which valve is comprised of a relatively fixed valve body 12 and a rotatable valve core 14, shown best in FIGS. 6 and 7. The valve core is rotatably mounted within the valve body and its position is manipulated by means of a valve handle 16. The handle includes three radially extending arms 18, 20 and 22 and a radial boss 24, all of which serve to provide gripping means for turning the valve as well as to provide an indication as to valve position and flow paths when taken in conjunction with the color coding arrangement to be described below. The valve parts preferably are fabricated from plastic and for this purpose the parts may be molded from plastics such as high density polyethylene, polycarbonate, or the like, to provide a snugly fitting assembly in which the core may be turned against a relatively high coefficient of friction between the parts so as to prevent the valve from being turned accidentally.

The valve body is hollow, cylindrical in cross-section, and closed at its bottom end. The valve body is provided with two inlet connection tubes 26 and 28 and one outlet connection tube 30. The inlet tube 26 is connected through a check valve 32 and a flexible length of tubing 34 to a first container of liquid medication comprising the primary IV set. The inlet tube 28, in turn, is connected via a check valve 36 and a length of flexible tubing 38 to a second container of medication and comprises the secondary IV set. The outlet tube 30 is connected via a check valve 40 and a length of flexible tubing 42 to the patient by means of a hollow needle inserted in the patient's vein and held in place by tape or other means.

The valve body, as previously indicated, is hollow, cylindrical in cross-section, and closed at its bottom end. The two inlet tubes 26 and 28 and the single outlet tube 30 are arranged 90° apart and connect with the interior of the body through ports open to the center of the valve body, as shown in FIG. 6. The valve core 14 is generally cylindrical and slightly tapered to rest snugly within the valve body. The valve body is formed near its upper end with an annular groove 44 to receive an annular rib 46 formed near the top of the valve core providing a sealing and positioning connection between the core and the body. The bottom portion of the core 14 has a circular recess 48 communicating with three ports 50, 52 and 54 spaced 90° apart and adapted to register with the two inlet tubes 26 and 28 and the outlet tube 30, depending upon the angular position of the valve core. By rotating the core from one position to another, either one or both of the inlet tubes may be connected to the outlet tube, or both inlets may be shut off to the outlet.

In order that the attendant supervising the administration of the medication through the primary and secondary IV sets may quickly determine the valve position and flow paths with absolute certainty, the valve body and valve handle are color coded in a way that simplifies and insures positive identification of valve position. In accordance with the invention, the inlet tubes 26 and 28 and the outlet tube 30 is each provided with a distinctive color code. In the preferred embodiment, the inlet tube 26, connected to the primary IV set, is colored with a green band throughout; while the inlet tube 28, connected to the secondary IV set, is colored blue, and the outlet tube 30, which connects to the patient, is colored red. The rotatable valve handle 16 is also color coded, and in the preferred embodiment the arm 18 is colored blue, the arm 20 is colored white, and the arm 22 is colored green, while the boss 24 is colored red. The arms 18, 20 and 22 are in alignment, respectively, with the ports 50, 52 and 54 formed in the valve core. The white arm 20 is opposite the red boss 24, while the blue arm 18 is opposite the green arm 22 in the manner shown. The inlet and outlet tubes, as well as the arms and boss, are shaded to designate the particular color coding.

Figure 2:
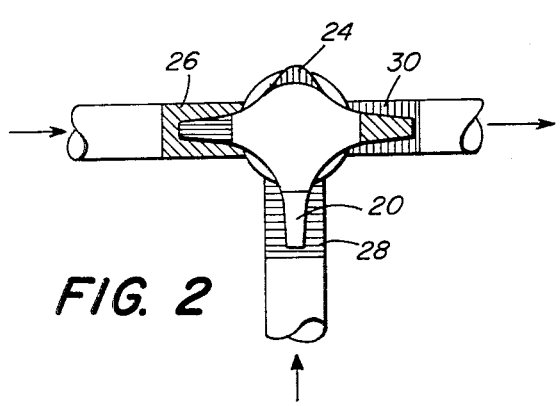
FIG. 2 is a top plan view thereof showing the valve with all lines open.

Referring more particularly to FIGS. 2, 3, 4 and 5, there is illustrated a sequence of views showing the valve in different operating positions and the color coding arrangement which allows the valve position to be readily identified. In FIG. 2, the valve handle is shown in a position where both the primary inlet 26 and the secondary inlet 28 are open as well as the outlet tube 30 so that both the primary and secondary medications are flowing into the patient. In this condition the valve handle is turned so that the colored components, red, white and blue, are in a straight line; namely, the red boss 24, the white handle arm 20, and the blue inlet tube 28 are in a straight line. Thus the operator seeing red, white and blue in a line will know immediately that all of the lines are open and all medications are flowing to the patient.

Figure 3:
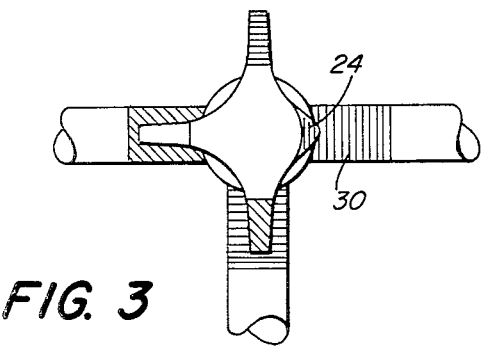
FIG. 3 is a view similar to FIG. 2 showing the valve in the full off position.

In FIG. 3, the valve handle has been turned 90° so that the red boss 24 is aligned with the red outlet tube 30 in which position the valve is in the off position, with neither the primary or secondary medications flowing to the patient. Thus, with red-on-red appearing to the attendant, he will immediately know that the value is in a fully off position.

Figure 4:
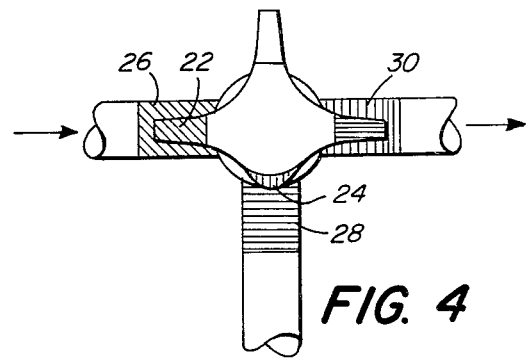
FIG. 4 is a view similar to FIG. 2 showing the valve with one line only open.

In FIG. 4, the valve handle has been turned another 90° so that the green valve handle arm 22 is aligned with the green primary inlet 26. In this position of the valve, medication flowing from the primary IV set will pass through the valve and through the outlet 30 to the patient. With the red boss 24 aligned with the blue secondary inlet 28, the red identifies that the secondary inlet is in the off position and no secondary medication will flow, while the green-on-green will immediately indicate to the operator that the green line is open and the primary medication only is flowing to the patient.

Figure 5:
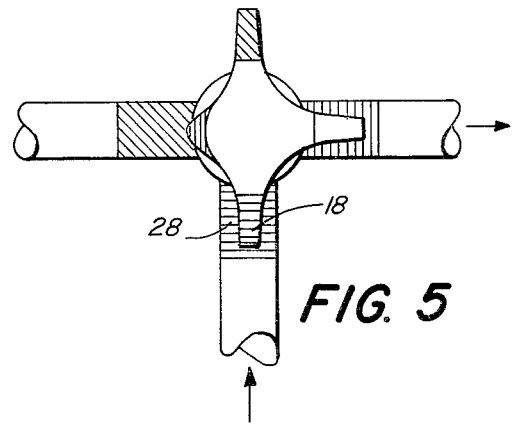
FIG. 5 is a view similar to FIG. 2 showing the valve with another line only open.

In the FIG. 5 valve position, the valve handle has been turned another 90°, in which position the primary medication line has been turned off while the secondary medication line has been turned on. The outlet line is maintained in the open position so that the secondary medication flowing through the inlet tube 28 will pass through the valve to the patient. In this position, the red hub has been aligned with the green primary inlet indicating that the primary set has been shut off, while the blue handle arm 18 is shown aligned with the blue inlet tube 28 connecting to the secondary IV set. Thus, with the blue-on-blue showing, the operator will immediately know that the secondary medication only is flowing to the patient. In each view, arrows are shown to illustrate the flow paths with different valve positions.

In order to prevent the unintentional back flow of medications or blood, either from the patient or from one IV set to the other, the check valves 32, 36 and 40 are provided. These check valves are designed to open in the normal or forward flow direction and to close in the event of any reverse flow of liquids. Each check valve, as best shown in FIG. 8, is comprised of a cylindrical housing 56, preferably of clear plastic, in which is mounted a small, lightweight, circular disc or valve element 58 having a flat face 60 on one side and peripheral protuberances 62 on the opposite side. Both ends of each check valve are open and each check valve is formed with the inner flat face 64 opposite the flat face 60 of the disc 58. Under normal flow conditions, medication passing through the line 34, for example, from the primary IV set will displace the valve disc 58 from the face 64, thereby opening the check valve. The opposite end of the check valve is kept open by virtue of the protuberances 62 which, in the open position, seat against the opposite flat face 66 within the check valve, with the medication flowing in and around the movable disc.

In the event of any reverse flow, the pressure on the opposite side of the disc 58 will cause the disc to unseat from the face 66 and seat against the opposite face 64, thereby shutting off the flow. The disc is quite light and responds to small pressure changes so as to open and close immediately, depending upon the flow direction. Insofar as both inlets and the outlet are provided with a check valve, no back flow can occur either from the blood line 52 to the patient or from one IV set to the other. Thus, the medications are kept separate and this prevents the flow of the medication in one line from mixing with the medication of the other line, which might otherwise occur.

The inlet check valves 32 and 36 are oriented so that the protrusions 62 on the disc 58 face towards the valve 10, in which position flow is permitted only in a direction into the valve which the check valve closing from any back pressure. The check valve 40 on the outlet side of the valve 10 is in the reverse position, with the protrusions facing downstream away from the valve 10 and towards the patient. Thus, the check valve 40 is open when the flow is towards the patient and closes in the event of any backflow towards the valve 10.

The check valve arrangement has several advantages, one of which is to prevent mingling of medications, particularly when the valve 10 is in the fully off position. Without the check valves, the medications in the primary and secondary sets could easily co-mingle as the result of a differential in pressure between the two lines. Such differential in pressure could occur where one IV bottle is suspended at a height above a second bottle.

Referring now to FIG. 9 of the drawings, there is illustrated a modification of the invention, and in this embodiment there is shown a ganged pair of color-coded, multi-position stop cock valves 10 and 10' that are connected to one another by means of a tubular conduit 70. The valve 10 is of the same configuration and color coding arrangement as the valve 10 described above, while the valve 10' is of a similar configuration and with the same color coding. However, the valve 10' is not provided with the check valves of the FIG. 1 embodiment, but is otherwise of similar construction. The valve 10' includes a valve handle 72 of the same configuration and color code arrangement as the handle 16 of the FIG. 1 embodiment and the valve body is provided with inlet tubes 74 and 76 and an outlet tube 78 corresponding in function and color with the inlet tubes 26 and 28 and outlet tube 30 of the principal embodiment.

The valve color coding is the same as in the principal embodiment, with the inlet tube 74 colored green, the inlet tube 76 colored blue, and the outlet tube 78 colored red. As before, when the red and white parts of the valve handle 72 are in a straight line with the blue inlet tube 76, the valve is in the fully open position, while a red-on-red alignment between the handle and the tube is a fully closed position of the valve. The inlet tubes 74 and 76 are opened selectively by aligning a similarly colored portion of the valve handle with the respective tube which is designed to be open.

In the FIG. 9 embodiment, the inlet tube 74 is connected through the tube 70 to the outlet tube 30 of the valve 10 so that, depending upon the position of the handle of the valve 10, one or two, or both, medications will be flowing through the line 70, or neither medication will be flowing if the valve is fully off. Assuming that the valve is in one of the open positions, the medication flowing through the valve 70 will pass through the inlet tube 74, and if the valve handle 72 with the valve 10' is in a position that connects the tube 74 to the outlet tube 78, the medication will flow through the valve 10' to the patient through a tube 80.

The tube 76 is fitted with an injection cap 82 by means of which an additional medication may be given to the patient without further puncturing of the patient's skin, or intravenous blood samples may be taken also without insertion of an additional needle in the patient. The cap 82, as best shown in FIG. 10, is comprised of a connector 84 and a rubber diaphragm 86 assembled thereto and engaging the end of the tube 76. The tube 76 is provided at its outer end with thread elements 88 to form a LUER-LOK connection with the connector 84. The connector 84 is a molded plastic piece formed with an outer skirt 90, the inner walls of which are threaded to engage the thread elements 88 when the parts are coupled to one another. The connector 84 is also provided with a central collar 92 which extends beyond the skirt and is dimensioned to fit into the open end of the tube 76. The collar is formed with a central passage 94 communicating with the outer end of the connector which is formed with an annular portion 96.

The diaphragm 86, typically fabricated from rubber, is formed with an outer annular skirt 98 which fits over the outer end of the connector and an inner annular skirt 100 which fits within the annular portion 96. The skirt 100 defines a center axial recess 102 which aligns with the passage 94 and terminates near the outer wall of the rubber cap. Medication is administered or venous blood samples obtained by means of a syringe 104, with the syringe needle 106 aligned with the center of the cap and pressed into the cap so that the needle punctures the rubber diaphragm and passes through the recess 102 and passage 104.

If the medication is not to be mixed with the other medications, or if a blood sample is to be taken, the valve handle 72 is turned so as to stop all flow from the line 70. This is done by aligning the red portion of the valve handle with the green tube 74, and with the blue portion of the handle aligned with the blue tube 76. If medication only is being administered, the needle 106 is inserted and the plunger of the syringe is depressed to the extent required. However, if a venous blood sample is being taken, the needle of an empty syringe would be inserted through the cap and one or two samples should first be drawn off before the final sample is taken in order to remove any medication residing in the IV set between the valve 10' and the patient. Since medication is cut off during this procedure, the blood will be drawn back up through the line 80 through the valve 10' and into the syringe without mixing with medication.

Figure 11:
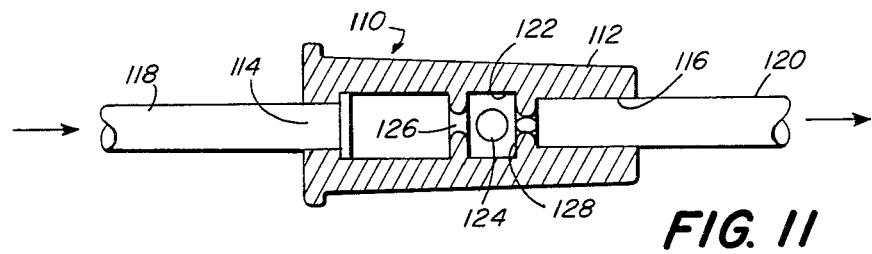
FIG. 11 is a detail sectional view of a modification of a check valve employed in the invention.

Referring now to FIG. 11 of the drawings, there is illustrated a modified check valve for use with the stop cock valve 10 in place of the check valve 32 shown in FIG. 8. the check valve of FIG. 11, as generally indicated by reference character 110, is comprised of a somewhat cylindrical body portion 112, preferably of a clear plastic material and formed with axial openings 114 and 116 at each end to receive the ends of flexible plastic tubes 118 and 120, or to connect directly to an inlet or outlet tube on a valve 10 as in the principal embodiment. The body 112 is also formed with a medial chamber 122, in which is mounted a small metal ball 124 mounted for limited movement between a restricted orifice 126 communicating with the opening 114 and a plurality of spaced radial bosses 128 defining a passage to the opening 116. The ball 124 is larger than either the orifice 126 or the gap between the bosses 128. The normal flow direction is shown by the arrows, and under normal flow conditions the ball 124 will be seated against the bosses 128 which, since they are spaced from one another, maintain an open flow path between the conduits 118 and 120. However, in the event of a back surge from the line 120, the ball 124 will immediately seat against the edges around the orifice 126, blocking off back flow into the line 118.

Figure 12:
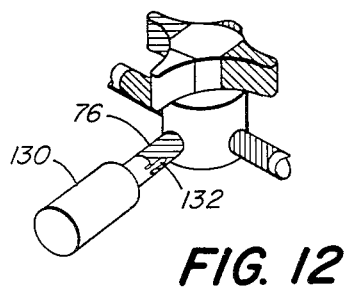
FIG. 12 is a view in perspective of an injection cap covered by a removable protective covering.
Figure 13:
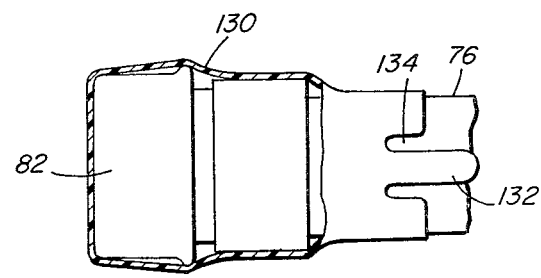
FIG. 13 is an enlarged side view thereof.

Referring now to FIGS. 12 and 13, there is illustrated a removable, protective cover 130 for use primarily on injection caps 82 as a means to maintain the cap in a sterile condition until such time as the cap is to be punctured to either withdraw a blood sample or to inject medication by means of a syringe. The cap 130 preferably is in the form of a thin plastic hood of a material that is impervious to bacteria and, in practice, is made of a heat shrinkable plastic material. The hood is fitted over the cap 82 and then heated in order to shrink the open end of the hood down against the neck of the inlet 76 to form a tight seal therewith. The cover 130, as shown in FIG. 13, is formed with a tab 132 extending from a re-entrant recess 134 along the inner edge of the covering. The covering is removed by grasping the tab 132 and pulling it back, causing the cover to tear for substantially the full length of the hood and allowing the hood to be pulled away for access to the diaphragm 86.

Figure 14:
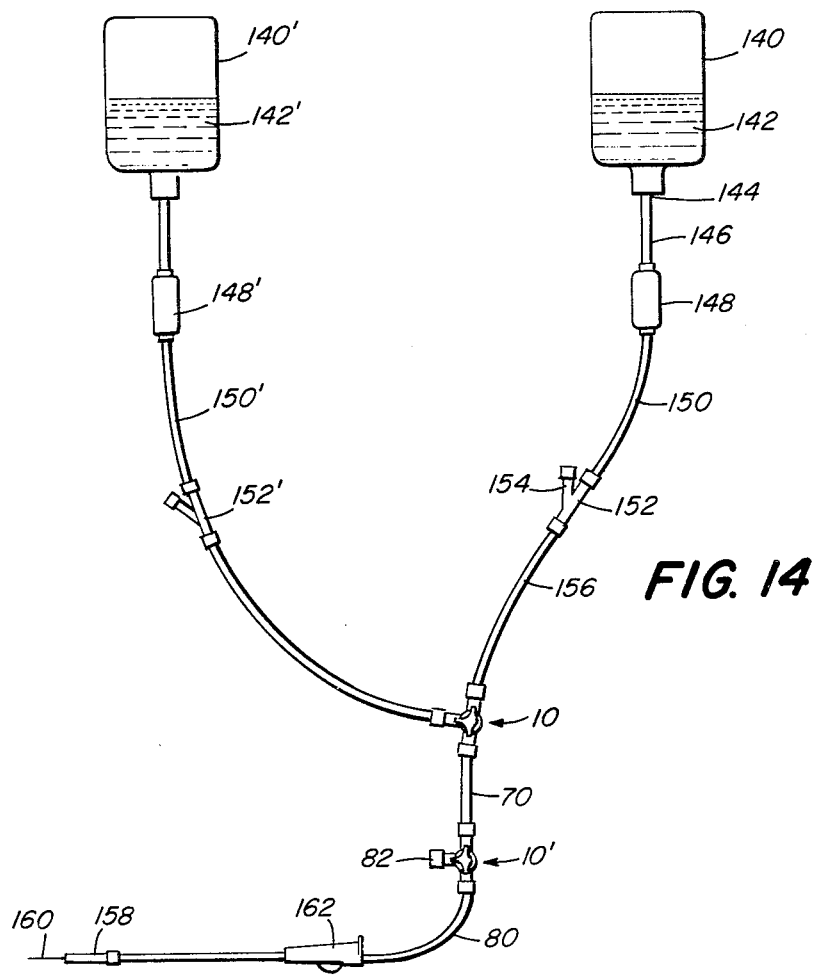
FIG. 14 is a view in perspective of an IV set made according to the invention.

In FIG. 14, there is illustrated a typical IV set-up utilizing components of the present invention. In the FIG. 14 embodiment, one IV set is connected to another IV set so that two medications may be delivered individually or simultaneously to a patient through the same needle. The primary IV set is comprised of a container 140 for a liquid medication 142 and suitably supported in an elevated position to allow the liquid 142 to be delivered by gravity flow. The container is supported in an inverted position and a connector plug 144 is attached to the neck of the container. Below the connector plug is a section of tubing 146 communicating with a drip chamber 148 which, in turn, is connected by a length of tubing 150 to a Y-injection fitting 152 which permits the coupling of additional IV sets, or the injection of other medication at a Y-stem 154. From the Y-fitting 152, a tubular section 156 connects to the color coded valve 10 of the principal embodiment and which, in turn, connects by means of the line 70 to the color coded valve 10'. From the valve 10', a flexible tube section 80 is connected to a needle adapter 158 equipped with a standard needle 160 which is inserted in the patient. An adjustable clamp 162 is provided along the tubing section 80 allowing control over the delivery rate of the medication flowing to the patient.

Having thus described the invention, what I claim and desired to obtain by Letters Patent of the United States is:

1. A multi-position valve, comprising
   (a) a relatively fixed valve body formed with at least three angularly spaced body passages for feeding fluids to and from said valve, said body having a different distinctive color thereon adjacent each of said passages;
   (b) a valve core mounted for relative angular movement in said body and formed with at least three angular spaced core passages adapted to form different flow paths according to the angular position of said core with respect to said valve body;
   (c) a handle on said core having at least four radial portions at different angular locations, all but one of said portions corresponding to said core passages;
   (d) each of said portions being uniquely and differently colored with respect to the other of said portions whereby flow paths through said valve may be identified by the color relation between said handle portions and said body passages;
   (e) at least three of said handle portions being of the same colors as at least three of said body passages whereby flow paths through said valve may be identified by aligning a portion of said handle with a correspondingly colored portion on said body;
   (f) the number of radial portions on said handle being one greater than the number of body passages and representing an extra radial portion being distinctly colored with respect to all other portions on said handle and on said body.

2. A multi-position valve, according to claim 1, in combination with a plurality of intravenous injection sets, said sets being connected to different body passages for delivery of separate fluids separately to said valve and a single conduit connected to an outlet passage of said body for delivering at least one of said fluids separately or combined according to the position of said handle.

3. A multi-position valve, according to claim 1 including a check valve connected to said body along each of said body passages, each check valve including a tubular housing formed with a passage therethrough, said passage having a reduced circular portion and a loose ball mounted in said passage and having a diameter in excess of the diameter of said reduced portion and adapted to close said passage when seated against said reduced portion, said housing being formed with spaced protuberances extending into said passage in spaced proximity to said reduced portion and trapping said ball therebetween.

4. A multi-position valve, according to claim 1 including a check valve connected to said body along each of said body passages, each check valve including a tubular housing formed with a relatively large chamber therein and a pair of coaxial passages communicating with opposite ends thereof, and a disc mounted for limited axial movement transversely in said chamber, said disc being formed with flat face on one side for closing said check valve when said flat face is against one end of said chamber and formed with a plurality of spaced protusions to maintain a flow path through said check valve when said disc is at the opposite end of said chamber.

5. A multi-position valve, according to claim 1, wherein said valve body is formed with a tubular extension extending outwardly from said body at each body passage for connection with a flexible tubular conduit for delivery of fluids to and from said valve.

6. A multi-position valve, according to claim 5, wherein each of said extensions terminates in LUER-LOK fitting for coupling said extensions to said conduits.

7. A multi-position valve, according to claim 1, in combination with a second multi-position valve of a construction similar to that of the first multi-position valve, a tubular conduit connecting an outlet body passage of said first valve to an inlet body passage of said second valve, and a flexible diaphragm cap closing another body passage of said second valve and adapted to be punctured by the needle of a syringe for injecting a fluid into said valve or withdrawing a sample therefrom.

8. A multi-position valve, according to claim 7, including a cover of a material impervious to bacteria tightly sealed over said cap and removable therefrom.

9. A multi-position valve, according to claim 8, wherein said cover terminates in an edge along which is formed a tab and re-entrant notches on both sides thereof for tearing away said cover.

10. A valve for use with intravenous injection sets, or the like, comprising
(a) a valve body formed with a chamber of circular cross-section and at least three angularly spaced inlet and outlet ports in said body communicating with said chamber and the exterior of said body;
(b) said body being formed with angularly spaced connecting means each formed with a passage communicating with one of said ports and connectable to a tubular conduit for feeding fluids to and from said valve, each connecting means being distinctly colored;
(c) a generally cylindrical valve core rotatably mounted in said chamber;
(d) said core being formed with passages adapted to form different flow paths between said ports, according to the angular position of said core;
(e) at least four outer arms on said core extending radially outwards therefrom in spaced angular relation to one another, and all but one extending in a direction corresponding to one of said flow paths;
(f) each of said arms being uniquely colored with respect to each other and at least three being of the same colors as the connecting means to form a color code whereby flow paths through said valve are identified by the color relation between said arms and said connecting means;
(g) the number of said arms being one greater than the number of said connecting means and representing an extra arm being distinctly colored with respect to all other arms and all of said connecting means.

* * * * *